US008845612B2

(12) United States Patent
Sebree et al.

(10) Patent No.: US 8,845,612 B2
(45) Date of Patent: Sep. 30, 2014

(54) METHODS FOR IONTOPHORETICALLY TREATING NAUSEA AND MIGRAINE

(75) Inventors: Terri B. Sebree, Gladwyne, PA (US); Mark Pierce, Essex, CT (US); Carol O'Neill, Phoenixville, PA (US)

(73) Assignee: NuPathe Inc., Frazer, PA (US)

( * ) Notice: Subject to any disclaimer, the term of this patent is extended or adjusted under 35 U.S.C. 154(b) by 108 days.

(21) Appl. No.: 12/853,922

(22) Filed: Aug. 10, 2010

(65) Prior Publication Data

US 2011/0066100 A1 Mar. 17, 2011

Related U.S. Application Data

(60) Provisional application No. 61/232,617, filed on Aug. 10, 2009, provisional application No. 61/256,796, filed on Oct. 30, 2009, provisional application No. 61/358,300, filed on Jun. 24, 2010.

(51) Int. Cl.
A61M 31/00 (2006.01)
A61K 9/70 (2006.01)
A61K 9/00 (2006.01)
A61K 31/42 (2006.01)

(52) U.S. Cl.
CPC ............ *A61K 31/42* (2013.01); *A61K 9/7023* (2013.01); *A61K 9/009* (2013.01)
USPC .......................................... 604/501

(58) Field of Classification Search
USPC .................................. 604/20, 501
See application file for complete search history.

(56) References Cited

U.S. PATENT DOCUMENTS

| 4,822,802 | A | 4/1989 | Levy et al. |
| 4,927,408 | A | 5/1990 | Haak et al. |
| 5,207,752 | A | 5/1993 | Sorenson et al. |
| 5,358,483 | A | 10/1994 | Sibalis |
| 5,458,569 | A | 10/1995 | Kirk, III et al. |
| 5,466,217 | A | 11/1995 | Myers et al. |
| 5,533,971 | A | 7/1996 | Phipps |
| 5,605,536 | A | 2/1997 | Sibalis |
| 5,651,768 | A | 7/1997 | Sibalis |
| 5,685,837 | A | 11/1997 | Horstmann |
| 5,697,896 | A | 12/1997 | McNichols et al. |
| 5,807,571 | A * | 9/1998 | List ................ 424/449 |
| 5,882,677 | A | 3/1999 | Kupperblatt |
| 5,941,843 | A | 8/1999 | Atanasoska et al. |
| 6,035,234 | A | 3/2000 | Riddle et al. |
| 6,090,095 | A | 7/2000 | McNichols et al. |
| 6,171,294 | B1 | 1/2001 | Southam et al. |

(Continued)

FOREIGN PATENT DOCUMENTS

WO WO-2007/120747 A2 10/2007
WO WO-2009/154649 A1 12/2009

OTHER PUBLICATIONS

National Headache Foundation 2008 Survey and Associated Symptoms.

(Continued)

*Primary Examiner* — Aarti B Berdichevsky
*Assistant Examiner* — Bradley Osinski
(74) *Attorney, Agent, or Firm* — McCarter & English, LLP; Danielle L. Herritt

(57) ABSTRACT

Methods for treating nausea and migraine by iontophoretically administering triptan compounds are provided.

18 Claims, 7 Drawing Sheets

(56) References Cited

U.S. PATENT DOCUMENTS

| | | | |
|---|---|---|---|
| 6,216,033 B1 | 4/2001 | Southam et al. | |
| 6,245,347 B1 | 6/2001 | Zhang et al. | |
| 6,416,503 B1 | 7/2002 | Suzuki et al. | |
| 6,421,561 B1 | 7/2002 | Morris | |
| 6,425,892 B2 | 7/2002 | Southam et al. | |
| 6,653,014 B2 | 11/2003 | Anderson et al. | |
| 6,745,071 B1 | 6/2004 | Anderson et al. | |
| 6,842,640 B2 | 1/2005 | Riddle et al. | |
| 6,975,902 B2 | 12/2005 | Phipps et al. | |
| 7,018,370 B2 | 3/2006 | Southam et al. | |
| 7,302,293 B2 | 11/2007 | Southam et al. | |
| 7,973,058 B2 * | 7/2011 | Anderson et al. | 514/323 |
| 2003/0013753 A1 | 1/2003 | Aung-Din | |
| 2003/0124179 A1 | 7/2003 | Jacobsen et al. | |
| 2004/0028721 A1 | 2/2004 | Colombo et al. | |
| 2004/0242770 A1 | 12/2004 | Feldstein et al. | |
| 2005/0148996 A1 | 7/2005 | Sun et al. | |
| 2005/0228336 A1 | 10/2005 | Keusch et al. | |
| 2006/0253061 A1 | 11/2006 | Anderson et al. | |
| 2007/0093788 A1 | 4/2007 | Carter | |
| 2007/0093789 A1 | 4/2007 | Smith | |
| 2009/0318847 A1 | 12/2009 | Sebree et al. | |

OTHER PUBLICATIONS

Brandes et al., "Sumatriptan-Naproxen Sodium for Migraine Treatment" JAMA 297(13): 1443-1454 (2007).

Buse et al., "*Frequent Nausea in Episodic Migraine (EM) is Common and Associated with Increased Burden: Results from the American Migraine Prevalence and Prevention (AMPP) Study*" Presented at the 2011 American Headache Society Annual Meeting.

Silberstein, Stephen D. "*Migraine Symptoms: Results of a Survey of Self-Reported Migraineurs*," Headache 35:387-396 (1995).

Goldstein et al., "Accepted Article", doi: 10.1111/j.1526-4610.2012.02198.x (American Headache Society 2012).

Femenia-Font et al. (Eur J. Pharmaceut and Biopharmaceut 61:50-55, 2005).

Fouchard et al. (J. Controlled Release 49:89-94, 1997).

Jadoul, Anne et al., "Transdermal Permeation of Alniditan by Iontophoresis: In Vitro Optimization and Human Pharmacokinetic Data," *Pharmaceutical Research*, vol. 13(9):1348-1353 (1996).

Jhee, Stanford S. et al., "Pharmacokinetics and Pharmacokynamics of the Triptan Antimigraine Agents," *Clin. Pharmacokinet.*, vol. 40(3):189-205 (2001).

Kalia, Y. et al., "Transdermal iontophoretic delivery of antimigraine therapeutics in vivo," *2004 AAPS Annual Meeting and Exposition*, (2004).

Lattin, Gary A. et al., "Electronic Control of Iontophoretic Drug Delivery," *Annals of the New Yorker Academy of Sciences*, vol. 618:450-464 (1991).

Patel, Sonal R. et al., "In vitro and in vivo evaluation of the transdermal iontophoretic delivery of sumatriptan succinate," *European Journal of Pharmaceutics and Biopharmaceutics*, vol. 66:296-301 (2007).

Patel, Sonal R. et al., "Transdermal iontophoresis of sumatriptan succinate in vitro," 205th Meeting, The Electrochemical Society, Inc., Abs. 725 (2004).

Patel, S.R. et al., "Transdermal iontophoretic delivery of sumatriptan in vitro," Cephalalgia, Abstracts of the 15th Migraine Trust International Symposium, (2004).

Preservative Directory. Household and Personal Products Industry, Pub. May 1, 2003.

International Search Report for application No. PCT/US2010/045045 dated Sep. 28, 2010.

Business Wire, "NuPathe reports positive phase one results for NP101 transderman ltherapy for acute migraine", New York, Jun. 8, 2007, printed from ProQuest data base on Oct. 23, 2010.

Pierce et al., Headache Relief, Drug Discovery & Development. May 1, 2008, (http://www.dddmag.com/Article-Anti-migraine-Drugs-Feature-New-Delivery-Methods.aspx Sep. 7, 2010) entire document esp. p. 1, para 7; p. 2, para 16.

ALZA Corporation (JNJ) Receives FDA Approval for IONSYS™ (Fentanyl Iontophoretic Transdermal System), retrievied online at http://www.biospace.com/news_story.aspx?NewsEntityId=19447&source=news-email (2006).

Anderson, Carter R. et al., "Effects of Iontophoresis Current Magnitude and Duration of Dexamethasone Deposition and Localized Drug Retention," *Physical Therapy*, vol. 83:161-170 (2003).

Anderson, Carter R. et al., "Quantification of Total Dexamethasone Phosphate Delivery by Iontophoresis," *International Journal of Pharmaceutical Compunding*, vol. 7(2):155-159 (2003).

Banga, Ajay K. et al., "Iontophoretic Delivery of Drugs: Fundamentals, Developments and Biomedical Applications," *Journal of Controlled Release*, vol. 7:1-24 (1988).

Chaturvedula, Ayyappa et al., "Dermal, Subdermal, and Systemic Concentrations of Granisetron by Iontophoretic Delivery," *Pharmaceutical Research*, vol. 22(8):1313-1319 (2005).

Chaturvedula, Ayyappa et al., "In vivo iontophoretic delivery and pharmacokinetics of salmon calcitonin," *International Journal of Pharmaceutics*, vol. 297:190-196 (2005).

Christensen, Michael L. et al., "Pharmacokinetics of Sumatriptan Nasal Spray in Adolescents," *J. Clin. Pharmacol.*, vol. 43:721-726 (2003).

Clariant Phenonip brochure, available at <http://www.thesoapkitchen.co.uk/-images/MSDS/preservatives/product_info_phenonip.pdf>, 2013.

Duquesnoy, C. et al., "Comparative clinical pharmacokinetics of single doses of sumatriptan following subcutaneous, oral, rectal and intranasal administration," *European Journal of Pharmaceutical Sciences*, vol. 6:99-104 (1998).

Femenía-Font, A. et al., "Iontophoretic Transdermal Delivery of Sumatriptan: Effect of Current Density and Ionic Strength," *Journal of PHarmaceutical Sciences*, vol. 94(10):2183-2186 (2005).

Pierce, M. et al., "NP101: A Novel Formulation of Sumatriptan Succinate Utilizing SmartRelief™ Transdermal Technology," 50th Annual Meeting American Headache Society, p. S46, No. S17 (2008).

Scholpp, J. et al., "Early treatment of a migraine attack while pain is still mild increases the efficacy of sumatriptan," *Cephalalgia*, vol. 24:925-933 (2004).

Siegel, Steven J. et al., "A Unique Iontophoretic Patch for Optimal Transdermal Delivery of Sumatriptan," *Pharmaceutical Research*, vol. 24(10):1919-1926 (2007).

Vyteris Announces Positive Results for Phase I Clinical Trial, Vyteris Holdings (Nevada), Inc. (2005).

Vyteris, "The smart patch by vyteris, The future of drug delivery . . . today!" JP Morgan 25th Annual Healthcare Conference (Jan. 2007).

Xu, Xiaohui et al., "Determination of degradation products of sumatriptan succinate using LC-MS and LC-MS-MS," *Journal of Pharmaceutical and Biomedical Analysis*, vol. 26:367-377 (2001).

International Search Report and Written Opinion for No. PCT/US07/09000, Oct. 13, 2008.

International Preliminary Examination Report for Application No. PCT/US08/81837, dated Jan. 30, 2009.

International Preliminary Examination Report for Application No. PCT/US08/81841, dated Jan. 22, 2009.

International Preliminatry Report on Patentability for Application No. PCT/US2010/045045, dated Feb. 14, 2012.

Rose, "Sumatriptan Arrests Migraine Aura" J. Roy Soc. Med. 84:519-521, 1992.

Benson et al., "Sumatriptan in the Treatment of Cyclic Vomiting" The Annals of Pharmoc., 29:997-999, Oct. 1999.

Lipton et al., "Effect of Rizatriptan and Other Triptans on the Nausea Symptom of Migraine: A Post Hoc Analysis" Headache, 41:754-763, 2001.

* cited by examiner

METHODS FOR IONTOPHORETICALLY TREATING NAUSEA AND MIGRAINE

RELATED APPLICATIONS

The present application claims the benefit of and priority to U.S. Provisional Application No. 61/232,617, filed Aug. 10, 2009, to U.S. Provisional Application No. 61/256,796, filed Oct. 30, 2009, and to U.S. Provisional Application No. 61/358,300, filed Jun. 24, 2010. Each of these provisional applications are incorporated herein in their entireties by this reference.

BACKGROUND

Migraine is a condition that affects approximately 28 million people in the United States, with females more frequently affected than males (Silberstein, *Neurology*, 2000 55:754-63). Migraine headache is associated with a painful vasodilation of cranial vessels that typically manifests in unilateral, pulsating pain of moderate or severe intensity that worsens with physical activity and typically lasts from 4 to 72 hours. In addition to headache pain, migraine can be associated with a variety of other symptoms including nausea, vomiting, phonophobia and photophobia (Lawrence, *Southern Medical Journal*, 2004, 97(11):1069-77). Approximately 20% of migraineurs experience an aura, which typically includes visual symptoms, such as spots of light, zigzag lines or a graying out of vision. Migraines may be triggered by a variety of factors, including stress, diet/foods, shifts in time schedules, body rhythms, sleep patterns, changes in weather/barometric pressure, changes in altitude and hormonal changes.

Mild migraine can sometimes be treated with over-the-counter medications such as aspirin, acetaminophen, non-steroidal anti-inflammatory drugs (NSAIDs) and combination products that include caffeine. Triptans may relieve up to 80% of migraines within two hours (Scholpp et al, *Cephalalgia*, 2004, 24:925-33). Seven different triptans have been approved and are currently marketed and are available in the United States in a variety of formulations, such as oral, dissolvable, nasal spray and injectable.

Sumatriptan is indicated for the acute treatment of migraine attacks, with our without aura, in adults. Sumatriptan is a serotonin agonist for a vascular 5-hydroxytriptamine$_{1D}$ (5-HT$_{1D}$) receptor subtype (a member of the 5-HT$_1$ family) and its therapeutic activity in migraine is generally attributed this agonist activity. Currently, it is available in three formulations: oral, injectable and nasal. While oral administration of sumatriptan tablets is typically well tolerated, oral administration suffers from inconsistent bioavailability and efficacy, partly due to variable presystemic hepatic metabolism. Injectable sumatriptan may be fast acting, but it is also short-lived. Sumatriptan nasal spray is more variable than the injectable form and is associated with side effects, e.g. bitter taste, which some patients find intolerable.

SUMMARY OF THE INVENTION

The present invention is based, at least in part, on the discovery that nausea and headache pain can be treated in a subject with migraine by iontophoretic delivery of a triptan compound without cardiovascular symptoms (e.g., symptoms that are typically associated with injectable delivery of a triptan) and also without migraine-associated absorption reduction (e.g., typically associated with oral delivery of a triptan during a migraine).

In some aspects, the present invention provides methods for treating nausea in a subject suffering from a migraine by iontophoretically administering an effective amount of a triptan compound to the subject, such that the nausea is treated without cardiovascular side effects.

In some embodiments, nausea is reduced in the subject by at least about 50%, e.g., by at least about 75%. In some embodiments, the nausea is treated without migraine-associated absorption reduction. In some embodiments, the migraine is aborted in the subject. In some embodiments, the nausea is treated without triptan side effects. In some embodiments, the nausea is treated for at least two hours. In some embodiments, the migraine is treated for at least two hours.

In some embodiments, the subject is suffering from a migraine with a pain severity score of 2 or 3. In some embodiments, the subject's headache score is reduced from a score of about 3 to about 2, to about 1, or to about 0. In some embodiments, the subject's headache score is reduced from a score of about 2 to about 1, or to about 0.

In some embodiments, the subject is a human. In some embodiments, the subject is suffering from migraine induced nausea or vomiting. In some embodiments, the subject is suffering from a prodromal migraine symptom, and the prodromal migraine symptom is treated. In some embodiments, the subject is suffering from a migraine aura, and the migraine aura is treated.

In some embodiments, the triptan compound is a sumatriptan or a pharmaceutically acceptable salt thereof.

In some embodiments, iontophoretically administering the triptan compound comprises a current which results in moderate, minimal or no erythema.

In some embodiments, the triptan compound is administered iontophoretically in a two phase manner, comprising:
  a first phase, wherein the triptan compound is administered with a current of about 4 mA for about an hour; and
  a second phase, wherein the triptan compound is administered with a current of about 2 mA for about three hours.

In some embodiments, the current does not substantially irritate the subject's skin. In some embodiments, the current does not result in a skin erythema score of greater than 2.5, of greater than 2.0, of greater than 1.5, or of greater than 1.0, immediately after patch removal.

DETAILED DESCRIPTION OF THE INVENTION

Figure 1:
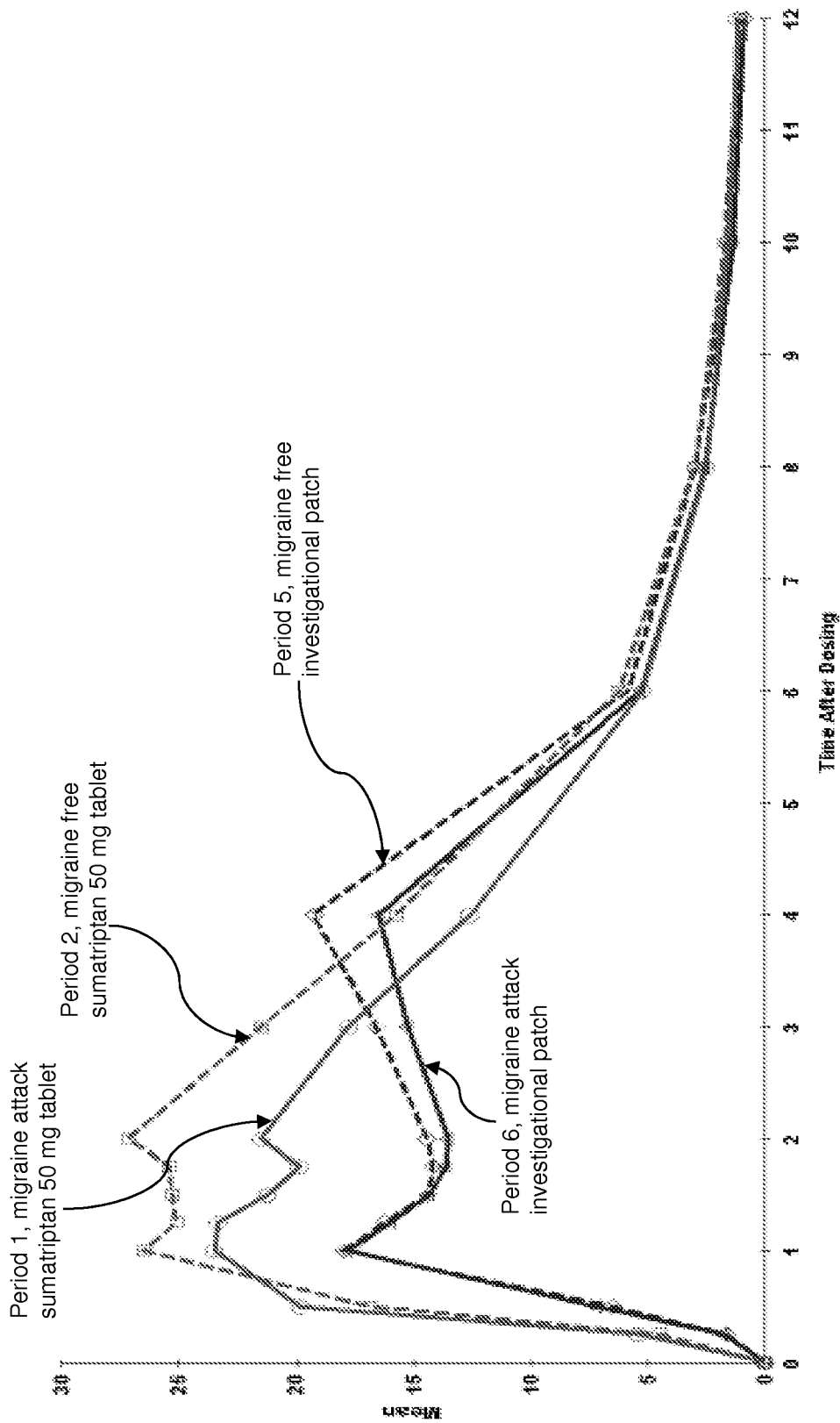
FIG. 1 is a graph illustrating the mean sumatriptan level (ng/mL) of all subjects from t=0 through 12 hours post-dosing of sumatriptan (50 mg) or the investigational iontophoretic patch administered during a migraine and in a migraine free period.

According to the National Headache Foundation, 55 percent of migraine sufferers can experience nausea as part of their migraine attacks. This often results in subjects delaying, modifying, or skipping treatment. Concerns about treatment side effects can also lead patients to delay, modify, or skip treatment in over one-third of migraine attacks. Moreover, many patients experience inconsistent relief, which can be attributed, in part, to substantial variation in oral drug absorption, particularly when the subject is suffering from a migraine. The present invention is based, at least in part, on the discovery that iontophoretic delivery of a triptan compound can treat a subject, e.g., a subject suffering from nausea, headache pain, etc., without cardiovascular symptoms, which are typically associated with injectable delivery of a triptan, and also without migraine-associated absorption reduction, which is typically associated with oral delivery of a triptan during a migraine. Without wishing to be bound by any particular theory, it is believed that iontophoretic administration as described herein can not only treat migraine, but also inhibit the start or progression of nausea in a subject suffering from migraine (for example by eliminating the need to swallow a pill), and even affirmatively reduce and/or treat nausea in migraine sufferers.

DEFINITIONS

In order to more clearly and concisely describe the subject matter of the claims, the definitions recited herein are intended to provide guidance as to the meaning of terms used herein.

As used herein, the articles "a" and "an" mean "one or more" or "at least one," unless otherwise indicated. That is, reference to any element of the present invention by the indefinite article "a" or "an" does not exclude the possibility that more than one of the element is present.

As used herein, the term "iontophoretically" or "iontophoretic" includes methods of administration which use electric current to promote the absorption of a triptan compound (e.g., sumatriptan) from the iontophoretic device (e.g., patch) through the skin of a subject.

Iontophoresis is a non-invasive drug delivery method that uses electrical current to move solubilized drugs across the skin to the underlying tissue. The technology typically employs the use of two electrodes with pads or reservoirs placed on top of each electrode with one containing the drug compound (e.g., the anode) and the other containing a salt solution (e.g., the cathode). Application of a low electrical potential across the electrodes results in the movement of ionized drug away from the electrode, through the skin and into the tissue. The quantity of drug transported into the skin is proportional to the total current delivered and is dependent upon a number of criteria, including the molecular weight of the drug ion, drug concentration and buffer concentration. The total current is typically expressed in units of milliamp minutes (mA min).

Since iontophoresis is a non-invasive process, there is no mechanical penetration or disruption of the skin. Using iontophoresis, therapeutic drug levels can be delivered parenterally without an injection. The rate and amount of drug delivery can be precisely controlled, so that doses may be automatically delivered, for example, in a pre-programmed manner. Thus, therapeutic drug levels can be delivered discretely over a specified period. Adverse events due to the iontophoresis process may include local erythema, irritation and pruritus. The extent to which these events occur is dependent on total current as well as the specific properties of the pharmaceutical agent being delivered.

The term "iontophoretic patch" or "iontophoretic transdermal patch" includes devices which allow for the iontophoretic administration of a triptan compound through the skin of a subject. In one embodiment, the patch comprises electrical components, a triptan compound and an adhesive backing layer. In a further embodiment, the iontophoretic patch may be an integrated device, e.g., wearable, self contained device that does not require a separate controller or power source. In another further embodiment, the iontophoretic patch of the invention is not integrated, e.g., requires a separate controller, power source, etc, and may not necessarily be wearable. Examples of iontophoretic patches may be found in U.S. Patent Application Publication Nos. 2009/00318847, 2009/0031745 and 2008/0287497 as well as U.S. Pat. No. 6,745,071. The contents of each of the foregoing are incorporated herein by reference.

The terms "treat" or "treatment" refer generally to the iontophoretic administration of a therapeutic agent (e.g., a triptan compound) to a subject. The subject generally has a disease or disorder, a symptom of disease or disorder or a predisposition toward a disease or disorder (e.g., a migraine). The purpose of treatment is generally to cure, heal, alleviate, relieve, remedy, ameliorate, or improve such disease, disorder, symptoms or predisposition. "Treated", as used herein, refers to the disease or disorder being cured, healed, alleviated, relieved, remedied, ameliorated, or improved. The terms "treat," "treated," "treating," or "treatment" include the reduction or amelioration of one or more symptoms of a migraine and/or the reduction or amelioration of nausea. It also may include the prevention of the occurrence or reoccurrence of the migraine and/or the nausea.

As used herein, the term "migraine" includes migraines with and without aura, basilar-type migraines, hemiplegic migraines, episodic migraines (e.g., those which occur less than about 15 times per month) and chronic migraines (e.g., those which occur more than about 15 times per month). As used herein, the term "migraine" includes migraines that are caused by one or more of the following triggers: hormonal changes, food, stress, sensory stimuli, changes in wake/sleep patterns, weather and barometric pressure changes, physical factors or medication.

The term "aborting a migraine," as used herein, includes the curtailing or substantial diminishment of one or more symptoms of a migraine after the subject has begun suffering from the migraine.

The term "prodromal migraine symptoms," as used herein, include symptoms that usually precede a migraine by several hours or day and that occur in approximately 40-60% of migraineurs. Prodromal migraine symptoms may include, but are not limited to, for example, altered mood, irritability, depression or euphoria, fatigue, yawning, excessive sleepiness, craving of certain foods, stiff neck, intestinal disturbances (e.g., constipation or diarrhea) and increased urination.

The term "migraine aura," as used herein, includes focal neurological phenomena that precede or accompany a migraine. The term "migraine aura" includes visual aura (e.g., photopsia, scintillating scotoma, blurred vision, tunnel vision and hemianopsia), somatosensory aura (e.g., digiolingual or cheiroral paresthesia), auditory or olfactory hallucinations, temporary dysphasia, vertigo, tingling or numbness of the face and extremities and hypersensitivity to touch.

The term "subject," as used herein, includes living organisms capable of having a migraine (with or without migraine-induced vomiting or nausea), a migraine aura or prodromal migraine symptoms (e.g., mammals). Examples of subjects include humans, pigs, primates, dogs, cats, horses, cows, goats, rats and mice.

As used herein, "triptan compound" refers to a member of the family of tryptamine-based drugs used as abortive medication in the treatment of migraines and cluster headaches. In some embodiments, triptan compounds include, for example, compounds of formula (I):

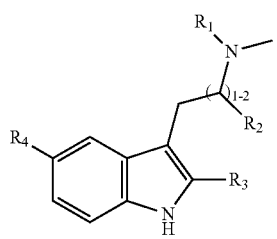

wherein:
$R_1$ is a C1-2 alkyl,
each occurrence of $R_2$ is H,
$R_3$ is H,
optionally $R_1$ and $R_2$ are connected by a C2-4 alkylene group to form a heterocyclic group including the nitrogen on the core;
optionally $R_2$ and $R_3$ are connected by a C2-4 alkylene group to form a cyclic group; and
$R_4$ is selected from C1-4 alkyl substituted with an amide, an N-methylamide, an N,N-dimethylamide, a sulfonamide, an N-methylsulfonamide, an N,N-dimethylsulfonamide, a pyrrolidinylsulfonyl, a benzylsulfonyl, a C1-4 alkylsulfonyl, a triazolyl, a pyrazolyl, a pyrrolyl, an oxazolidinonyl, an oxazolyl or an oxazolidinyl.

The term "triptan compound," as used herein, includes, for example, sumatriptan, rizatriptan, naratriptan, zolmitriptan, eletriptan, almotriptan and frovatriptan.

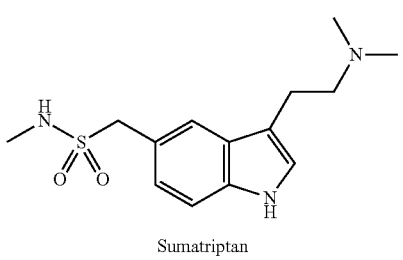

Sumatriptan

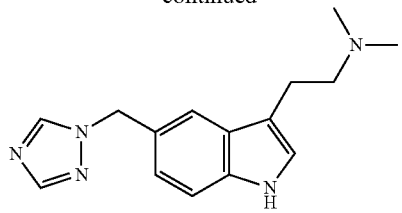

Rizatriptan

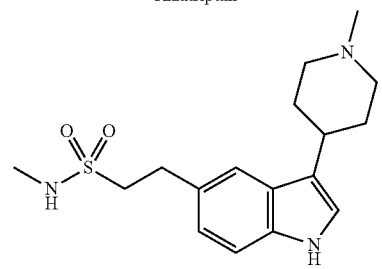

Naratriptan

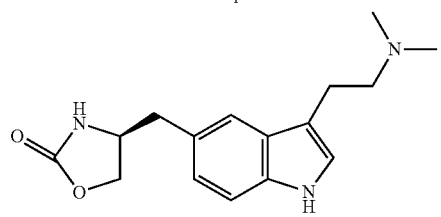

Zolmitriptan

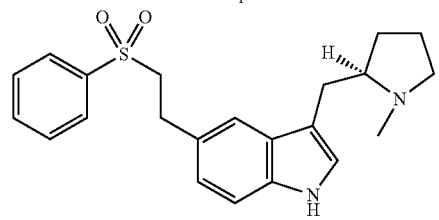

Eletriptan

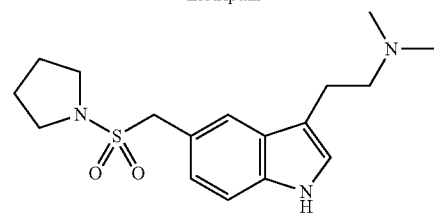

Almotriptan

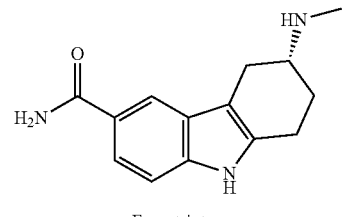

Frovatriptan

The term triptan compound also includes derivatives, analogs, prodrugs and pharmaceutically acceptable salts of the foregoing compounds. In one embodiment, the triptan compound is sumatriptan or a pharmaceutically acceptable salt thereof.

As used herein, the term "effective amount" refers to the amount of the triptan compound necessary to achieve a desired effect. The term "desired effect" refers generally to any result that is anticipated by the skilled artisan when the compounds described herein are administered to a subject. The term "effective amount" includes the amount of a triptan compound that is effective to treat a nausea in a subject suffering from a migraine. The term "effective amount" can also include the amount of a triptan compound that is effective, e.g., for treating a migraine, for treating nausea and/or for aborting a migraine in a subject suffering from a migraine. The term "effective amount" can further include the amount of a triptan compound that is effective for treating a subject suffering from prodromal migraine symptoms or migraine aura.

In some aspects, the present invention provides methods for treating nausea in a subject suffering from a migraine by iontophoretically administering to the subject an effective amount of a triptan compound.

In other aspects, the present invention provides methods for treating nausea and headache pain in a subject suffering from a migraine by iontophoretically administering an effective amount of a triptan compound to the subject.

In some embodiments, the methods of the present invention provide treatment of migraine or nausea (e.g., headache pain relief or nausea relief) for at least about 1 hour, at least about 2 hours, at least about 3 hours, at least about 4 hours, at least about 6 hours, at least about 8 hours, at least about 10 hours, at least about 12 hours, at least about 14 hours, at least about 16 hours, at least about 18 hours, at least about 20 hours, at least about 22 hours, or at least about 24 hours. In some embodiments, the methods of the present invention provide treatment of migraine and nausea (e.g., headache pain relief and nausea relief) for at least about 1 hour, at least about 2 hours, at least about 3 hours, at least about 4 hours, at least about 6 hours, at least about 8 hours, at least about 10 hours, at least about 12 hours, at least about 14 hours, at least about 16 hours, at least about 18 hours, at least about 20 hours, at least about 22 hours, or at least about 24 hours. In some embodiments, the methods of the present invention provide treatment of migraine and nausea (e.g., headache pain relief and nausea relief) for at least about 2 hours.

In some embodiments, nausea is reduced by about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or even about 100%. In some embodiments, nausea is reduced by about 50%. In some embodiments, nausea is reduced by about 75%. In some embodiments, nausea is reduced by about 100%. Reduction in nausea may be compared, for example, to nausea experienced prior to administration of the triptan compound.

In some embodiments, the triptan compound administered to the subject is sumatriptan or a pharmaceutically acceptable salt thereof, e.g., sumatriptan succinate.

Administration of triptans, e.g., intravenous administration of sumatriptan, can lead to a number of unwanted side effects. Such side effects may include, but are not limited to, palpitation, changes in blood pressure, sinusitis, tinnitus, allergic rhinitis, upper respiratory inflammation, ear, nose, and throat hemorrhage, external otitis, hearing loss, nasal inflammation, sensitivity to noise, sclera, mydriasis, blindness and low vision, visual disturbances, eye edema and swelling, eye irritation and itching, accommodation disorders, external ocular muscle disorders, eye hemorrhage, eye pain, keratitis, conjunctivitis, diarrhea, gastric symptoms, anemia, myalgia, phonophobia, photophobia, dyspepnea, hypersensitivity, coronary artery vasospasm, myocardial infarction, ventricular tachycardia and ventricular fibrillation. Without wishing to be bound by any particular theory, it is believed that the present invention provides a means for administration of a triptan compound which allows for effective treatment of nausea and/or migraine, while minimizing triptan side effects. In some embodiments, the present invention provides methods for treating nausea and/or migraine without triptan side effects. As used herein, the term "triptan side effects" refers to the side effects experienced by a subject receiving a triptan compound, and includes those discussed immediately above. In some embodiments, the subject does not suffer from side effects comparable to the side effects suffered by subjects receiving intravenous administration of sumatriptan.

Administration of triptans, e.g., intravenous administration of sumatriptan, can lead to cardiovascular side effects. Such side effects include, for example, palpitations, syncope, changes in blood pressure, arrhythmia, changes in ECG, hypertension, hypotension, pallor, pulsating sensations, tachycardia, and in more rare cases, angina, atherosclerosis, bradycardia, cerebral ischemia, cerebrovascular lesion, heart block, peripheral cyanosis, thrombosis, transient myocardial ischemia, and vasodilation. Without wishing to be bound by any particular theory, it is believed that the present invention provides a means for administration of a triptan compound which allows for effective treatment of nausea and/or migraine, while minimizing cardiovascular side effects. In some embodiments, administration of the triptan compound utilizing the methods provided herein does not cause cardiovascular side effects. As used herein, the term "cardiovascular side effects" refers to the cardiovascular side effects experienced by a subject receiving intravenous sumatriptan, and includes those discussed immediately above. In some embodiments, the present invention provides relief from nausea and/or migraine with no cardiovascular side effects.

In some embodiments, the present invention provides methods for treating nausea and/or migraine in a subject susceptible to cardiovascular side effects. Without wishing to be bound by any particular theory, it is believed that certain subpopulations of migraine sufferers are susceptible to cardiovascular side effects (e.g., when administered a triptan compound intravenously). The iontophoretic methods described herein can treat nausea and/or other migraine symptoms in subjects susceptible to cardiovascular side effects such that the nausea and/or other migraine symptoms are treated without cardiovascular side effects.

The methods of the present invention can allow triptan compounds to be administered such that the $AUC_{0-inf}$ is comparable to that of other dosage forms such as systemic, oral or nasal administration, while the $C_{max}$ is substantially reduced or eliminated. By doing this, the amount of triptan compound delivered systemically may be comparable to the other methods, but concentration spiking is significantly reduced. That is, in some embodiments, the methods of the present invention provide an effective amount of sumatriptan such that migraine and/or nausea are treated, while minimizing or preventing concentration spiking or burst such that side effects, e.g., those described herein, are also minimized or prevented. Another advantage of the methods of the present invention is that the concentration of triptan compound in the subject generally reaches therapeutic levels less than an hour after administration begins. Furthermore, therapeutic levels of triptan compound may be maintained for a desired length of time, e.g., four to five hours.

In other embodiments, the present invention provides methods for aborting a migraine in a subject having a migraine. In some embodiments, the present invention provides methods for treating a subject suffering from prodromal migraine symptoms by iontophoretically administering an effective amount of a triptan compound to the subject. In other embodiments, the present invention provides methods for treating a subject suffering from a migraine aura comprising iontophoretically administering an effective amount of a triptan compound to the subject. In some embodiments, the present invention provides methods for relieving headache pain in a subject with migraine.

The subject may be any of those described herein. In one embodiment, the subject is a human. In a further embodiment, the subject may be suffering from a migraine (with or without migraine-induced vomiting or nausea), a migraine aura or prodromal migraine symptoms. In other embodiments, the subject is suffering from nausea or vomiting that may or may not be migraine-induced. In yet another embodiment, the subject suffering from migraine has a pain severity score of 2 or 3 (see Table 1, infra). In still other embodiments, the subject's pain severity score is reduced from a score of about 3 to about 2, to about 1 or to about 0 after iontophoretic administration as described herein. In other embodiments, the subject's pain severity score is reduced from a score of about 2 to about 1 or to about 0 after iontophoretic administration as described herein. In a further embodiment, the subject has a history of suffering from migraines (with or without vomiting or nausea), prodromal migraine symptoms or migraine aura. In some embodiments, the subject is susceptible to cardiovascular side effects or migraine effect.

The methods of the present invention may be advantageous over oral and/or nasal administration of triptan compounds because there is less variation of pharmacokinetic parameters with the present invention as compared to oral or nasal delivery. For example, in contrast to oral delivery of sumatriptan, the amount of variance between the subjects after being administered sumatriptan iontophoretically is a fraction of the amount of variance between the subjects after being administered sumatriptan orally. Additionally, also in contrast to oral delivery of sumatriptan, the amount of variance between individual iontophoretic administrations of sumatriptan in a single subject is a fraction of the amount of variance between individual oral administrations of sumatriptan to a single subject.

In some embodiments, the methods of the present invention provide treatment of nausea and/or migraine without migraine-associated absorption reduction. As used herein, the term "migraine-associated absorption reduction," which may also be referred to herein as "migraine effect," refers to a reduction in the amount of absorption of a drug, e.g., a triptan compound, into the plasma of a subject suffering from a migraine (with or without migraine-induced vomiting or nausea) as compared to the amount of absorption of the drug into the plasma of the subject during a migraine free period. In one embodiment, the migraine-associated absorption reduction is a reduction in the amount of absorption of sumatriptan. In one embodiment, the migraine-associated absorption reduction is a reduction in the amount of absorption of orally administered sumatriptan. Without wishing to be bound by any particular theory, it is believed that migraine-associated absorption reduction may be due, at least in part, to the effect of a migraine on the ability of the gastrointestinal tract to absorb the drug (e.g., the sumatriptan).

In some embodiments, the present invention provides methods for treating nausea and/or migraine in a subject susceptible to migraine-associated absorption reduction. Without wishing to be bound by any particular theory, it is believed that certain subpopulations of migraine sufferers are susceptible to migraine-associated absorption reduction (e.g., when administered a triptan compound orally). The iontophoretic methods described herein can treat nausea and/or other migraine symptoms in subjects susceptible to migraine-associated absorption reduction such that the nausea and/or other migraine symptoms are treated without migraine-associated absorption reduction.

In some embodiments, the iontophoretically administered triptan compound provides about a 5%, about a 10%, about a 15% about a 20%, about a 25%, about a 30%, about a 35% or about a 40% greater triptan plasma level (e.g., $C_{max}$) in the subject post administration compared to the triptan plasma level in the subject upon oral administration of a triptan compound in a therapeutically effective amount (e.g., sumatriptan in a 50 mg oral dose). In some embodiments, an iontophoretically administered 6 mg of sumatriptan provides about a 5%, about a 10%, about a 15% about a 20%, about a 25%, about a 30%, about a 35% or about a 40% greater sumatriptan plasma level in the subject post-administration compared to the sumatriptan plasma level in the subject upon oral administration of 50 mg of sumatriptan.

In some embodiments, an effective amount of the triptan compound is iontophoretically administered. In one embodiment, the effective amount is about 6 mg of a triptan compound (e.g., sumatriptan). That is, in some embodiments, the methods for iontophoretic administration of a triptan compound provide about 6 mg of the triptan compound to a subject. In another embodiment, the effective amount of sumatriptan is greater than about 5 mg, greater than about 10 mg, or greater than about 15 mg. For example, in some embodiments, the effective amount is about 6 mg of a triptan compound per iontophoretic patch. In one embodiment, the effective amount of the triptan compound is effective to treat a migraine. In one embodiment, the effective amount of the triptan compound is effective to treat nausea. In some embodiments, the effective amount of sumatriptan provides a concentration of about 10 ng/mL or greater, about 11 ng/mL or greater, about 12 ng/mL or greater, about 13 ng/mL or greater, about 14 ng/mL or greater, about 15 ng/mL or greater, about 16 ng/mL or greater, about 17 ng/mL or greater, about 18 ng/mL or greater, about 19 ng/mL or greater, about 20 ng/mL or greater, about 21 ng/mL or greater, about 22 ng/mL or greater, or about 22.5 ng/mL or greater in the subject's blood or plasma. In a further embodiment, the effective amount of sumatriptan provides about 10 to about 25 ng/mL in the subject's plasma.

In some embodiments, iontophoretic administration of the effective amount of the triptan compound provides a $C_{max}$ of about 20 ng/mL with a $T_{max}$ of about 2 hours. The terms "$C_{max}$" and "$T_{max}$" are pharmacokinetic parameters that are defined as the maximum observed drug concentration and the time from $T_0$ to maximum drug concentration, respectively. In other embodiments, iontophoretic administration of the effective amount of the triptan compound provides an $AUC_{0-12}$ of between about 98 and about 103 hr*ng/mL. The term "$AUC_{0-12}$" is a pharmacokinetic parameter that is defined as the area under the concentration versus time curve from time 0 to the 12 hour time point, calculated using linear trapezoid rule.

In yet other embodiments, iontophoretic administration of the effective amount of a triptan compound provides a steady state triptan plasma level of greater than or about equal to about 10 ng/mL beginning before about 1 hour post-administration and lasting between about 4.5 and about 5.0 hours (e.g., about 4.7 hours) post-administration. The term "steady state," as used herein, is defined as the rate at which the rate of administration of the triptan compound is substantially about equal to the rate of elimination of the triptan compound from the subject's body. The terms "triptan plasma level" or "triptan plasma concentration" include the concentration of the triptan compound in the plasma of the subject. In one embodiment, the terms "triptan plasma level" and "triptan plasma concentration" include sumatriptan plasma levels and sumatriptan plasma concentrations.

In some embodiments, the $AUC_{0-4}$ (e.g., the area under the concentration versus time curve from time 0 to the 4 hour time point, calculated using linear trapezoid rule) or $C_{max}$ of the triptan compound administered iontophoretically is substantially about the same as the $AUC_{0-4}$ or $C_{max}$ of a triptan compound administered orally in a therapeutically effective amount (e.g., 50 mg or 100 mg oral sumatriptan).

In some embodiments, the subject's triptan plasma concentration reaches between about 10 and about 20 ng/mL within 1 hour after iontophoretic administration of the triptan compound and is maintained between about 10 and about 20 ng/mL for at least 3 hours after iontophoretic administration of the triptan compound. In other embodiments, the subject's triptan plasma concentration is between about 15 and about 20 ng/mL (e.g., about 17 ng/mL) about 1 hour after iontophoretic administration of the triptan compound. In yet other embodiments, the subject's triptan plasma concentration is between about 10 and about 15 ng/mL (e.g., about 14 ng/mL or about 15 ng/mL) about 2 hours after iontophoretic administration of the triptan compound. In still other embodiments, the subject's triptan plasma concentration is between about 15 and about 20 ng/mL (e.g., about 15 ng/mL or about 16 ng/mL) about 3 hours after iontophoretic administration of the triptan compound. In yet other embodiment, the subject's triptan plasma concentration is between about 15 and 20 ng/mL (e.g., about 16 ng/mL or about 19 ng/mL) about 4 hours after iontophoretic administration of the triptan compound.

In some embodiments, the triptan compound is administered iontophoretically in a two phase manner. In some embodiments, the two phase manner includes a first phase which lasts between about thirty minutes and about two hours, between about thirty minutes and about ninety minutes, or about one hour. The first phase, in some embodiments, employs a current of between about 3.5 mA and about 4.5 mA, between about 3.75 mA and about 4.25 mA, about 4.0 mA. In some embodiments, the two phase manner includes a second phase which lasts between about 2 hours and about 6 hours, between about 2 hours and about 5 hours, between about 2 hours and about 4 hours, or about three hours. The second phase, in some embodiments, employs a current of between about 1.5 to about 2.5 mA (e.g., about 2 mA). In another embodiment, the triptan compound is administered iontophoretically in a first phase wherein the triptan compound is administered with a current of about 4 mA for about an hour; and a second phase wherein the triptan compound is administered with a current of about 2 mA for about three hours.

In other embodiments, the current selected in the methods provided does not substantially irritate the subject's skin. As used herein, the term "does not substantially irritate a subject's skin" includes a resulting skin erythema score of about 2.5 or less, about 2.0 or less, about 1.5 or less or about 1.0 or less upon patch removal. In one embodiment, the current "does not substantially irritate a subject's skin" if the skin erythema score of about 2.5 or less, about 2.0 or less 1.5 or less, or about 1.0 or less within 2 hours of patch removal. In another embodiment, the current "does not substantially irritate a subject's skin" if the skin erythema score is about 2.5 or less, about 2.0 or less, about 1.5 or less or about 1.0 or less immediately upon patch removal. Skin erythema scores may be found in Table 2, infra. Accordingly, in some embodiments, the methods of the present invention utilize a current which results in moderate, minimal or no erythema. In some embodiments, the methods of the present invention utilize a current which results in no or minimal erythema. In some embodiments, the methods of the present invention utilize a current which results in no or minimal erythema in over 85%, (e.g., over 86%, over 87%, over 88%, over 89%, over 90%, over 91%, over 92%, over 93%, over 94%, over 95%, over 96%, over 97%, over 98%, over 99%) of a patient population.

In other embodiments, the current does not result in a skin erythema score of greater than about 2.5, of greater than about 2.0, of greater than about 1.5 or of greater than about 1.0 immediately after patch removal. In some embodiments, the current results in moderate, minimal or no erythema. In some embodiments, the current results in minimal or no erythema.

EXEMPLIFICATION OF THE INVENTION

The methods of this invention can be understood further by the following examples. It will be appreciated, however, that these examples do not limit the invention. Variations of the invention, now known or further developed, are considered to fall within the scope of the present invention as described herein and as hereinafter claimed.

Example 1

A Phase I, Open Label, Single Dose, Four-Way Crossover Study Comparing the Pharmacokinetics of a Sumatriptan Iontophoretic Transdermal Patch with an Oral Formulation of Imitrex® (50 mg) in Migraine Subjects During an Acute Migraine Attack and During a Non-Migraine Period Objective: The primary objective of this Phase I study was to compare the pharmacokinetics (PK) of a sumatriptan iontophoretic transdermal patch with a currently approved formulation of Imitrex® in migraine subjects both during an acute migraine attack and during a non-migraine period.

Methodology/Study Design: This was a Phase I, open label, single-dose, four-way crossover study. Screening assessments were performed during the Screening (prior to Period 1) and Re-Screening (prior to Period 5) visits.

In Period 1, when the subject experienced a migraine headache, they arrived at the clinic. To qualify for Period 1, the subject's headache was moderate (score of 2) or severe (score of 3) in pain intensity, using the Subject's Headache Pain Severity Score found in Table 1. Additionally, the subject arrived at the clinic within approximately 4 hours of the onset of their migraine and the subject had no food or alcohol intake in the prior 4 hours. Triptans, opioids, ergotamines, drugs affecting gastric motility (i.e., metoclopramide, anti-emetics) were prohibited within 72 hours of arrival at the clinic.

TABLE 1

| Score | Definition |
|---|---|
| 0 | No pain |
| 1 | Mild pain: allowing normal activity |
| 2 | Moderate pain: disturbing, but not preventing normal activity |
| 3 | Severe pain: normal activity has to be discontinued, bed rest may be necessary |

If the subject met the eligibility criteria, they underwent PK sampling following dosing with Treatment A (sumatriptan succinate, RT Technology™, Imitrex® tablet: 50 mg taken orally). Rescue medications were allowed after the last PK sample was obtained.

In Period 2, during a non-migraine period, the subject returned to the clinic. To qualify for Period 2, the subject must not have headache or aura, and the subject's last migraine headache must have been resolved at least 72 hours prior to clinic arrival. Additionally, the subject had no prodromal symptoms for at least 24 hours prior to the trial, and no food or alcohol intake in the prior 4 hours. Triptans, opioids, ergotamines, drugs affecting gastric motility (i.e., metoclopramide, anti-emetics) were prohibited within 72 hours of arrival at the clinic.

If the subjects met the additional criteria, they underwent PK sampling following dosing with Treatment A.

Once Periods 1 and 2 were completed, and data collected regarding oral sumatriptan therapy, Periods 3, 4, 5 and 6 commenced. These periods were designed to provide data regarding iontophoretic sumatriptan therapy. In Periods 3 and 4, the investigational sumatriptan iontophoretic transdermal patch may have been exposed to freezing conditions during shipping. Periods 5 and 6 were added to the protocol and all subjects who participated in Periods 3 and 4 were invited to participate in Periods 5 and 6, a replication of Periods 3 and 4.

In Periods 3 and 6, subjects arrived at the clinic when they experienced a migraine headache. If the subject met the additional eligibility criteria regarding timing of headache onset, headache severity, food and alcohol intake and medication restrictions (see Period 1), they underwent PK sampling following dosing with Treatment B (investigational sumatriptan iontophoretic transdermal patch applied to the arm and left in place for 4 hours). The patch was designed to deliver approximately 6 mg of sumatriptan, utilizing 4 mA for one hour followed by 2 mA for three hours for a total of 600 mA minutes. Rescue medications were allowed after the last PK sample was obtained.

In Periods 4 and 5, during a non-migraine period, if the subject met the additional eligibility regarding the absence of migraine symptoms, food and alcohol intake and medication restrictions (see Period 2), they underwent PK sampling following dosing with Treatment B.

During Periods 1 to 4, fifteen blood samples were obtained at prescribed times for PK analysis. During Periods 5 and 6, fourteen blood samples were obtained at prescribed times for PK analysis. While wearing the investigational patch for periods 3, 4, 5 and 6, a patch adherence evaluation was performed by the investigative staff.

During Periods 2, 4 and 5 (non-migraine periods), a 24-hour urine sample was collected.

During Periods 3 and 4, a skin irritation examination was performed following treatment with the investigational patch at pre-dose, 4 hours (immediately following patch removal), 6, 12, 24, 48 and 72 hours post patch application. During Periods 5 and 6, a skin irritation examination was performed following treatment with the investigational patch at pre-dose, 4 hours (immediately following patch removal), 6, 12, 48 and 72 hours post patch application. If erythema was present at 72 hours, the subject returned to the clinic in 7 days (±1 day) for an additional skin irritation examination. If erythema was present at the Day 10 visit, the subject returned for weekly visits until the skin irritation score was 0.

The skin irritation examination was an assessment of the skin directly under the drug reservoir pad and directly under the salt reservoir pad. The skin irritation examination scale is presented in Table 2.

TABLE 2

| Score | Definition |
|---|---|
| 0 | No erythema |
| 1 | Minimal erythema |
| 2 | Moderate erythema with sharply defined borders |
| 3 | Intense erythema with or without edema |
| 4 | Intense erythema with edema and blistering/erosion |

Pharmacokinetic Serum Samples: Blood samples (4 mL per sample, a total of 60 mL for each Periods 1-4 and 28 mL for both Periods 5 and 6) for PK analysis were collected for all treatments for the determination of sumatriptan concentrations in plasma (analyzed by validated HPLC with MS/MS detection). During Periods 1 to 4, samples were taken at pre-dose (within 15 minutes prior to dosing) and at 0.25, 0.50, 1, 1.25, 1.5, 1.75, 2, 3, 4, 6, 8, 10, 12, and 24 hours post-dose. During Periods 5 and 6, the samples were the same, except the 24 hour post dose sample was omitted. Dose timing for Treatment A began when the oral tablet was swallowed and Treatment B began when the investigational patch was applied and the red LED light was continuously lit.

Selection of Study Populations:

Inclusion Criteria: Subjects must have met all of the following criteria:

1. Adult male and female subjects, between 18 and 65 at the time of the screening.
2. Subjects with a diagnosis of migraine headache, with or without aura, as defined in Section 1.1 and 1.2.1 of the International Classification of Headache Disorders, $2^{nd}$ Edition and the diagnosis was made before the age of 50.
3. Subjects typically experienced moderate (score of 2) or severe (score of 3) (refer to Table 1) headaches during a migraine attack (if untreated), based on subject testimony; and a majority of these attacks were accompanied by nausea and vomiting.
4. Subject had at least 1 year history of migraine based upon subject testimony.
5. Subject was judged to be in good health, based upon the result of a medical history, physical examination, vital signs, ECG and laboratory profile. Subjects did not have any clinically significant abnormal laboratory parameters, vital signs or ECG parameters on order to qualify for enrollment.
6. Subjects were capable of reading and understanding English or Spanish and were able to carry out all study procedures and voluntarily sign and date an Informed Consent agreement approved by an Institutional Review Board.
7. Subjects had a negative drug screen.
8. Female subjects of childbearing potential had a negative pregnancy test at the Screening.
9. Subject had two acceptable patch application sites (left and/or right arms) that were relatively hair free and had no scars, tattoos, scratches or bruises.

Test Products, Dose and Modes of Administration: The test product (Treatment B) was a transdermal patch with anode and cathode reservoir pads delivering approximately 6 mg of sumatriptan using a low electrical current to produce a waveform of 4 mA for 1 hour, then 2 mA for 3 hours utilizing a total of 600 mA minutes.

The drug reservoir pad (anode) formulation contained 3.0 grams of sumatriptan gel solution (10% polyamine and 4% sumatriptan succinate) containing 120 mg of sumatriptan succinate.

The salt reservoir pad (cathode) formulation was 3.0 grams of 2% hydroxypropylcellulose (HPC) solution with 0.9% NaCl.

Subjects who were invited to participate in all 6 periods of the study received 4 investigational patches, with 2 given during an acute migraine attack and 2 given during a non-migraine period.

Reference Therapy, Dose and Administration: The Reference Therapy was Treatment A (one formulation of RT Technology™ Imitrex® 50 mg oral sumatriptan tablet). Each subject received 2 tablets of the reference therapy: one given during an acute migraine and one tablet given during a non-migraine period.

Patch Adherence Evaluation: A patch adherence evaluation was performed for each patch treatment at 1, 2, 3 and 4 hours after patch application. The 4 hour evaluation was performed immediately before the patch is removed. Table 3 indicates the Patch Adherence Scoring Code to be used for this evaluation.

TABLE 3

| Score | Definition | Action Secure with Approved Adhesive Tape |
|---|---|---|
| 0 | ≥90% adhered (essentially no lift off of the skin) | n/a |
| 1 | ≥75% to <90% adhered (some edges only lifting off skin) | Yes |
| 2 | ≥50% to <75% adhered (less than half the patch lifting off the skin) | Yes |
| 3 | <50% adhered but not detached (more than half the system lifting off the skin without falling off | Yes |
| 4 | Patch detached (patch completely off the skin) | Yes |

Pharmacokinetic Parameters for Evaluation: The following PK parameters were calculated from the actual plasma concentration-time data using non-compartmental methods with WinNonlin: $AUC_{0-last}$, $AUC_{0-inf}$, $C_{max}$, $T_{max}$, $\lambda_z$ and $t_{1/2}$. Additional exploratory PK parameters were estimated, including $AUC_{0-2}$, $AUC_{0-4}$, time to achieve 10 ng/mL sumatriptan plasma concentrations and time to achieve 70%, 80% and 90% of $C_{max}$. Amount and percent of the drug excreted in the urine unchanged or as sumatriptan metabolites in urine over a 24-hour period was calculated from the 24-hour urine collection data during the non-migraine periods.

Pharmacokinetics: There were two populations for pharmacokinetic (PK) analysis. The first PK populations was the All PK Population that included all subjects who received at least one dose of study drug and who had sufficient plasma concentration-time data to derive the required PK parameters. The second PK analysis population was the PK Evaluable Population that included all subjects in the All PK Population who completed all 6 periods of the study. The PK Evaluable Population was the primary population for the investigational patch evaluation.

Results: A total of 23 subjects completed the oral and patch dosings. 23 subjects received at least one dose of oral sumatriptan (Treatment A) and 19 subjects received at least one iontophoretic patch application. All 23 subjects who received study treatment were included in the analyses of safety and pharmacokinetics. 18 subjects completed Periods 1, 2, 5, and 6, and were thus included in the analyses that compared pharmacokinetic parameters across treatments and/or periods.

The mean sumatriptan plasma levels (ng/mL) of all subjects over 12 hours post dosing is shown in FIG. 1.

Figure 3:
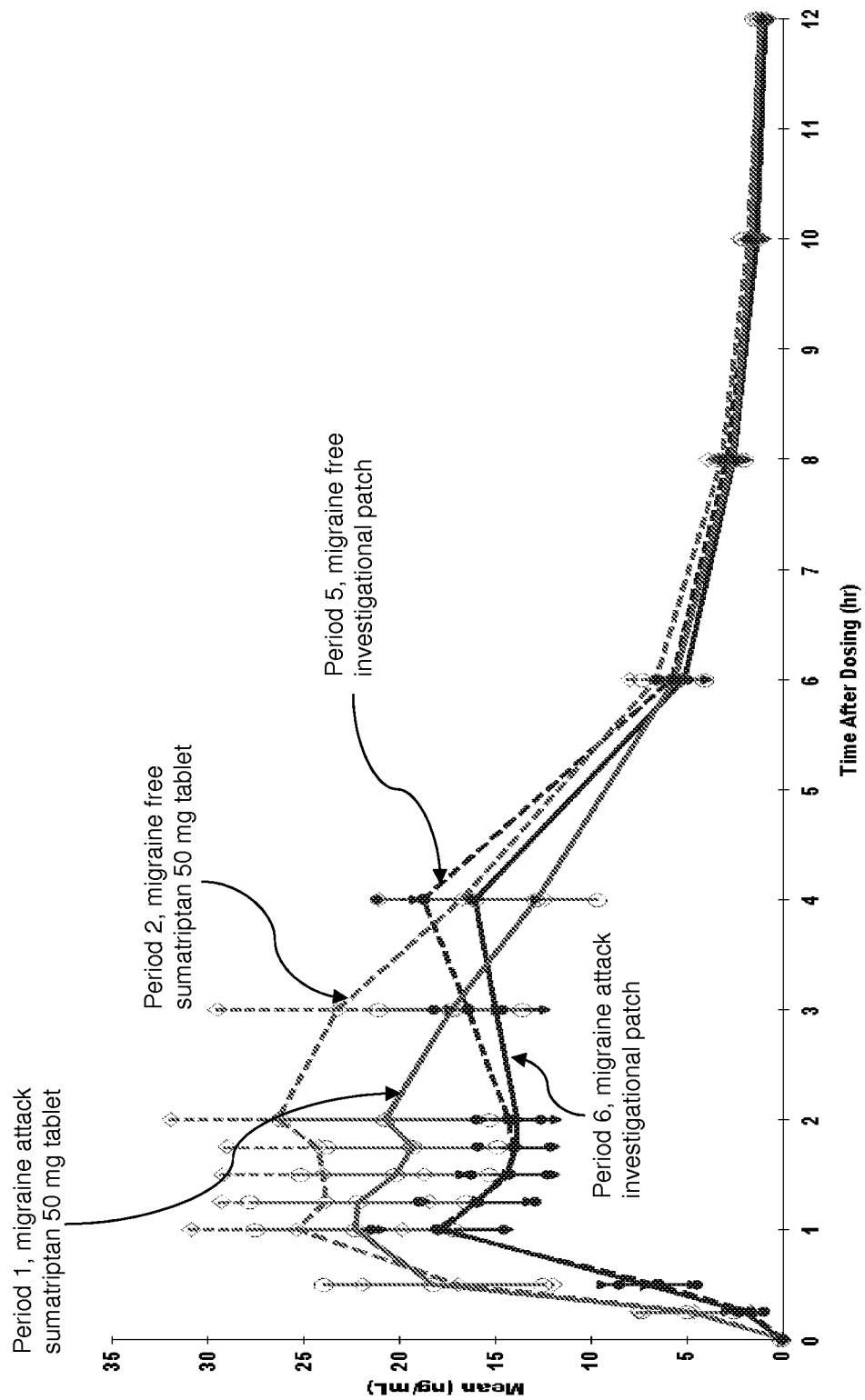
FIG. 3 is a graph illustrating the mean sumatriptan (95% CI) plasma concentration-time profile of the PK Evaluable Subjects (N=18) by treatment and period in linear scale.
Figure 4:
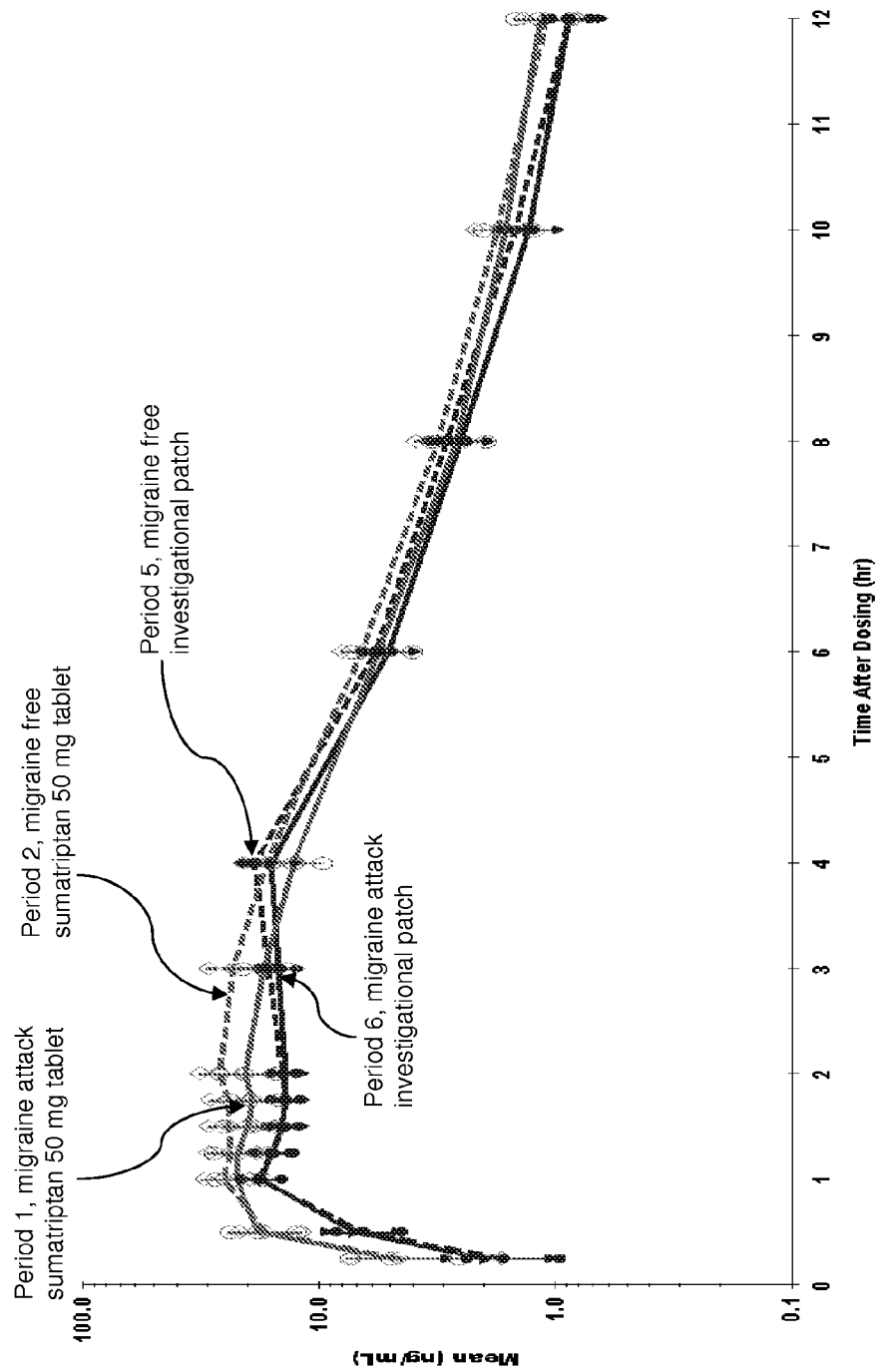
FIG. 4 is a graph illustrating the mean sumatriptan (95% CI) plasma concentration-time profile of the PK Evaluable Subjects (N=18) by treatment and period in semi-log scale.

Mean plasma concentration over time profiles for PK Evaluable subjects (i.e., subjects who participated in Periods 1, 2, 5, and 6) and the corresponding 95% confidence intervals (CIs) at each time point are shown in FIG. 3 (linear scale) and FIG. 4 (semi-log scale). Tables 4 and 5 provide a summary of the pharmacokinetic parameters $C_{max}$, $AUC_{0-4}$, $AUC_{0-12}$, $AUC_{0-inf}$, $T_{max}$, $t_{1/2}$, Time Above 10 ng/mL, and AUC above 10 ng/mL for Periods 1, 2, 5, and 6 in these subjects.

TABLE 4

Mean (SD) $C_{max}$ and AUC Values by Period and Treatment

| Period (Treatment/Migraine Status) | $C_{max}$ (ng/mL) | $AUC_{0-4}$ (hr · ng/mL) | $AUC_{0-12}$ (hr · ng/mL) | $AUC_{0-inf}$[1] (hr · ng/mL) |
|---|---|---|---|---|
| Period 1 (Oral/Migraine) | 26.3 (11.77) | 68.5 (28.74) | 102.1 (40.57) | 113.7 (47.34)[2] |
| Period 2 (Oral/Migraine-free) | 33.0 (12.36) | 83.1 (28.98) | 124.1 (41.81) | 138.3 (48.07)[b] |
| Period 5 (NP101/Migraine-free) | 21.1 (4.66) | 55.5 (13.70) | 95.4 (22.40) | 98.3 (23.26) |
| Period 6 (NP101/Migraine) | 20.0 (5.46) | 52.6 (15.34) | 87.5 (27.93) | 90.5 (29.22) |

[a]The last PK sample was taken 12 hours after dosing in Periods 5 and 6 whereas the last PK sample was taken at 24 hours after oral dosing in periods 1 and 2.
[b]One subject was excluded from $AUC_{0-inf}$ summary due to poor linearity of the terminal phase (% AUC extrapolation >20%).

TABLE 5

Mean (SD) $T_{max}$, $t_{1/2}$, Time Above 10 ng/mL, and AUC above 10 ng/mL Values by Period and Treatment

| Period (Treatment/Migraine Status | $T_{max}$ (hr) | $T_{1/2}$ (hr) | Time Above 10 ng/mL (hr) | AUC Above 10 ng/mL (hr · ng/mL) |
|---|---|---|---|---|
| Period 1 (Oral/Migraine) | 1.4 (1.23) | 5.6 (3.35)[1] | 3.8 (1.92) | 37.7 (25.44) |
| Period 2 (Oral/Migraine-free) | 1.8 (0.75) | 5.3 (2.63)[a] | 4.4 (1.31) | 53.1 (32.86) |
| Period 5 (NP101/Migraine-free) | 2.2 (1.47) | 2.2 (0.31) | 4.4 (0.84) | 26.9 (15.90) |
| Period 6 (NP101/Migraine) | 1.9 (1.37) | 2.3 (0.39) | 3.8 (1.70) | 23.6 (15.71) |

[a]One subject was excluded from $t_{1/2}$ summary due to poor linearity of the terminal phase (% AUC extrapolation >20%).

The data in FIGS. 1, 3 and 4 indicate that the mean sumatriptan plasma levels for all of the subjects for the administration of sumatriptan via the investigational patch was comparable for administration during a migraine (Period 6), as well as during a migraine free period (Period 5). In contrast, there was approximately a 20% reduction in the mean sumatriptan plasma levels during the first 4 hours after oral administration of sumatriptan during a migraine attack (Period 1) when compared to the oral administration of sumatriptan during a migraine free period (Period 2). The $AUC_{0-4}$ and $C_{max}$ were reduced by ≥about 20% during a migraine attack compared to the migraine free period. The difference in the mean sumatriptan plasma levels in the orally administered sumatriptan may be evidence of a "migraine effect," e.g., an absorption reduction. Without being bound by theory, some migraineurs may experience a reduction in absorption of sumatriptan orally administered during a migraine attack (versus when the subject is headache- or migraine-free), perhaps due in part to migraine-induced nausea or vomiting.

Figure 2:
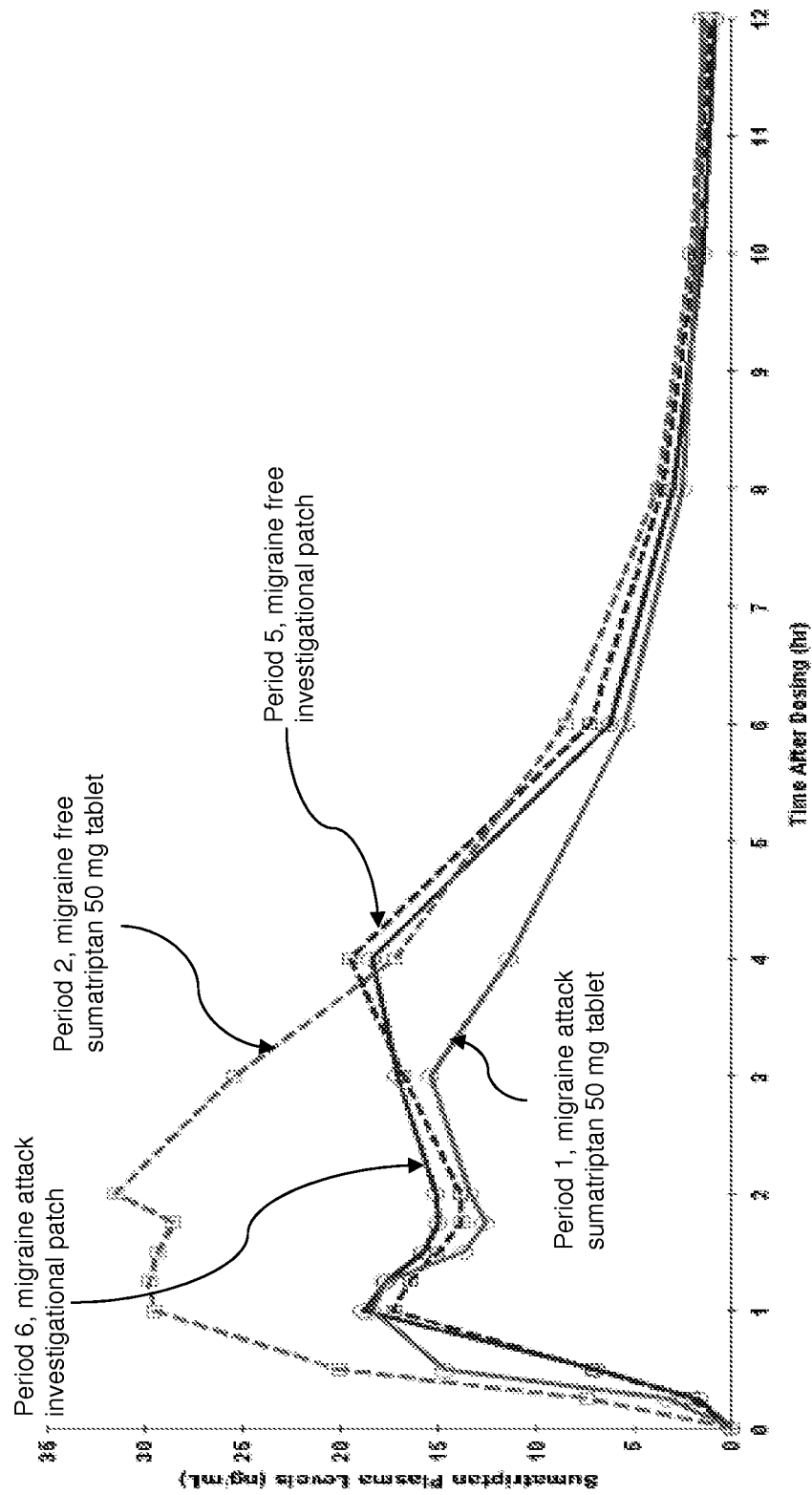
FIG. 2 is a graph illustrating the mean sumatriptan level (ng/mL) of the subjects exhibiting the migraine effect from t=0 through 12 hours post-dosing of sumatriptan (50 mg) or the investigational iontophoretic patch administered during a migraine and in a migraine free period.

The mean sumatriptan plasma levels for these subjects are represented in FIG. 2 and Table 6, below.

TABLE 6

| Mode of Administration | Approximate Sumatriptan Plasma Levels (ng/mL) over 12 Hours Post-Dosing | | | | | | | |
|---|---|---|---|---|---|---|---|---|
| | 1 hour | 1.75 hours | 2 hours | 3 hours | 4 hours | 6 hours | 8 hours | 12 hours |
| Period 1 (migraine attack, 50 mg suma. tablet) | 18 | 13 | 14 | 15 | 12 | 6 | 5 | 1 |
| Period 2 (migraine free, 50 mg suma. tablet) | 29 | 28 | 32 | 25 | 17 | 9 | 5 | 1 |
| Period 5 (migraine free, patch) | 17 | 14 | 14 | 16 | 18 | 10 | 5 | 1 |
| Period 6 (migraine attack, patch) | 18 | 15 | 15 | 16 | 17 | 10 | 5 | 1 |

Figure 5:
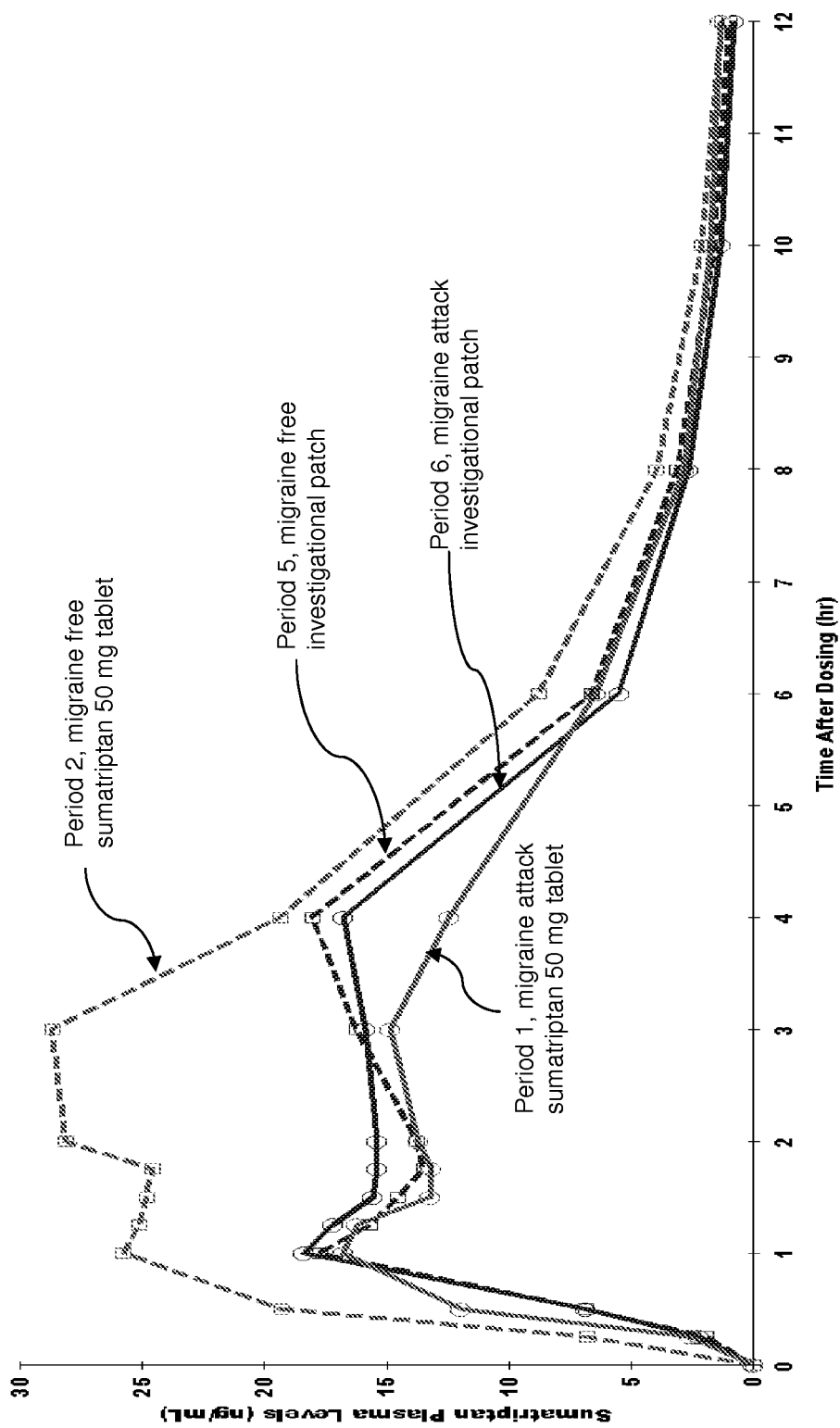
FIG. 5 is a graph illustrating the mean sumatriptan (95% CI) plasma concentration-time profile of the PK Evaluable Subjects with migraine effect following oral sumatriptan treatment (N=7) by treatment and period in linear scale.
Figure 6:
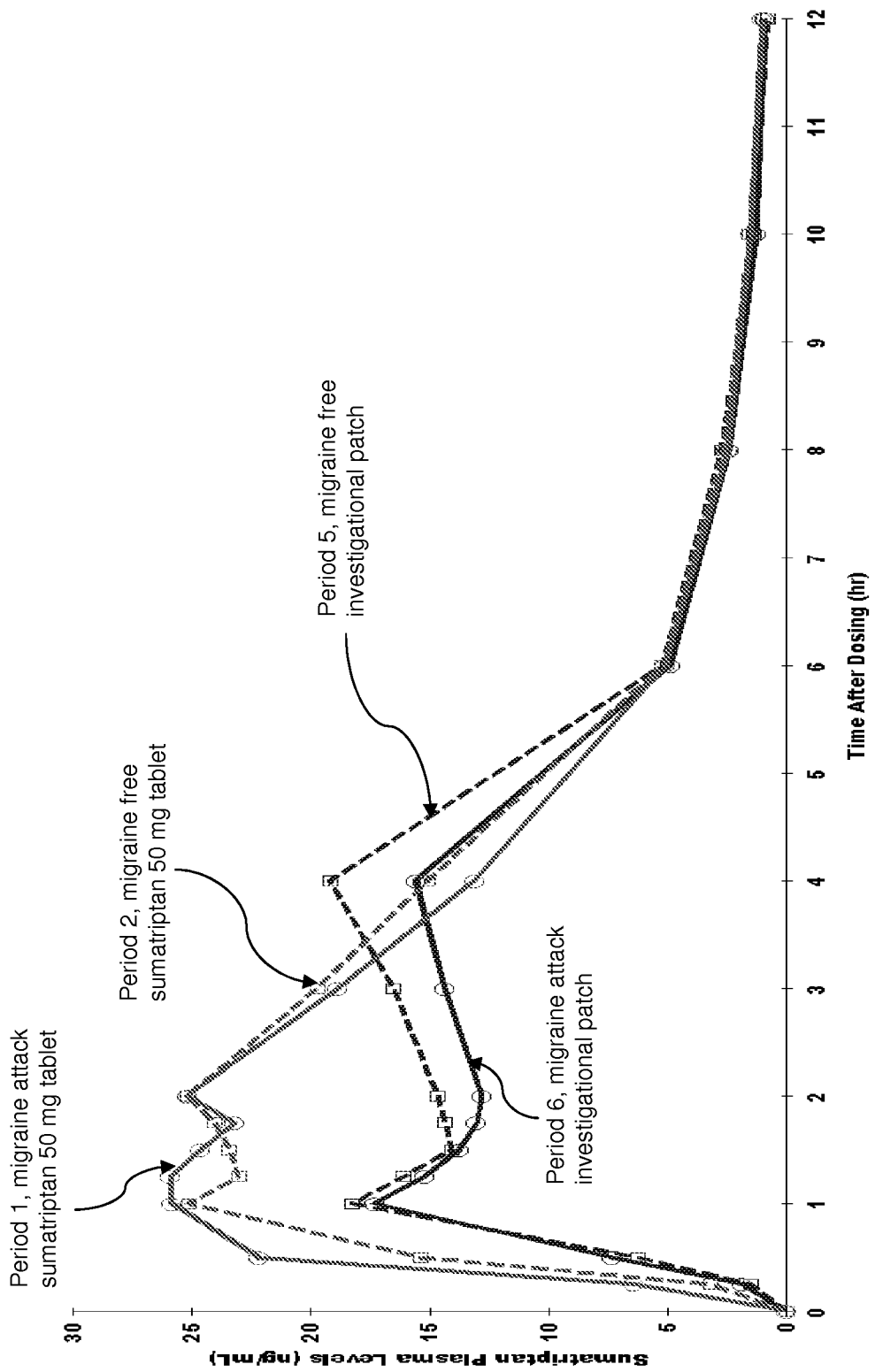
FIG. 6 is a graph illustrating the mean sumatriptan (95% CI) plasma concentration-time profile of the PK Evaluable Subjects without migraine effect following oral sumatriptan treatment (N=11) by treatment and period in linear scale.

The pharmacokinetic data for the subjects with the "migraine effect" is found below, in Table 7. Moreover, the mean plasma concentration-time profiles for subjects without the migraine effect following oral sumatriptan treatment and for those with the migraine effect following oral sumatriptan treatment are shown by period in FIG. 5 and FIG. 6, respectively.

The mean $T_{max}$, $t_{1/2}$ and time of plasma sumatriptan concentrations above 10 ng/mL did not appear to be affected by migraine after either oral sumatriptan or after patch. Following oral administration, the mean AUC above 10 ng/mL was somewhat higher during the migraine-free period (53.1 hr·ng/mL) than during the migraine period (37.7 hr·ng/mL).

The reduced exposure phenomenon (e.g., absorption reduction or migraine effect) was further quantified by comparing the ratio of exposure based on $C_{max}$ and $AUC_{0-4}$. That is, a subject was considered as having a significant migraine effect if the ratio of exposure was less than 80% for both $C_{max}$ ($C_{max(migraine)}/C_{max(migraine\ free)}$<0.80) and $AUC_{0-4}$ ($AUC_{0-4(migraine)}/AUC_{0-4(migraine\ free)}$<0.80). Of the 18 PK Evaluable subjects, seven subjects (39%) met this definition and were classified as having a significant migraine effect following oral sumatriptan treatment, while the remaining 11 subjects were classified as not having a significant migraine effect following oral sumatriptan treatment.

Among the seven subjects who demonstrated a migraine effect on absorption after oral treatment, there was a 48% decrease in mean $C_{max}$, a 45% decrease in mean $AUC_{0-4}$, a 39% decrease in mean $AUC_{0-12}$, and a 38% decrease in mean $AUC_{0-inf}$ during a migraine compared to a non-migraine period. The mean time above 10 ng/mL was also reduced during a migraine period (3.0 hours) compared to during a migraine-free period (5.1 hours). However, following patch treatment (Periods 5 and 6), there was no difference in absorption for the migraine period compared to the migraine-free period among these subjects. The mean time above 10 ng/mL was 4.6 hours and 4.3 hours during Periods 5 and 6, respectively.

For the 11 subjects who did not demonstrate a migraine effect following oral sumatriptan treatment, there were no marked differences in $C_{max}$ and AUC values between migraine and non-migraine periods after either oral administration or after NP101 patch treatment.

Two subjects had ratios of exposure that met the definition of a migraine effect after administration of the exemplary patch of the invention. Neither of these subjects met the criteria for a migraine effect with oral sumatriptan administration. For the remaining 16 PK Evaluable subjects, there were no marked differences in mean $C_{max}$ or $AUC_{0-4}$ for the migraine period compared to the migraine-free period following NP101 treatment.

Both study treatments were well tolerated in this study. There were no serious adverse events. The only adverse events reported after patch treatment were application site conditions in eight (42.1%) subjects. Except for two events of application site pruritus that were of moderate severity, all of

TABLE 7

| Period (Treatment/ Migraine Status) | $C_{max}$ (ng/mL) Migraine Effect | | $AUC_{0-4}$ (hr · ng/mL) Migraine Effect[a] | | $AUC_{0-12}$ (hr · ng/mL) Migraine Effect[a] | | $AUC_{0-inf}$ (hr · ng/mL) Migraine Effect[a] | |
|---|---|---|---|---|---|---|---|---|
| | Yes | No | Yes | No | Yes | No | Yes | No |
| Period 1 (Oral/Migraine) | 19.1 (10.76) | 30.9 (10.30) | 51.7 (35.36) | 79.2 (18.16) | 87.0 (53.22) | 111.7 (28.92) | 96.5 (64.91) | 123.1 (34.69) |
| Period 2 (Oral/Migraine-free) | 36.8 (13.20) | 30.5 (11.77) | 93.2 (34.44) | 76.7 (24.48) | 143.7 (39.95) | 111.6 (39.68) | 156.8 (45.69) | 125.4[b] (47.59) |
| Period 5 (NP101/Migraine-free) | 21.1 (2.59) | 21.1 (5.74) | 54.6 (8.20) | 56.0 (16.67) | 96.4 (12.19) | 94.8 (27.63) | 99.5 (12.87) | 97.5 (28.61) |
| Period 6 (NP101/Migraine) | 19.4 (3.14) | 20.4 (6.66) | 56.1 (12.28) | 50.5 (17.21) | 92.6 (23.63) | 84.3 (31.00) | 94.8 (24.31) | 87.7 (32.80) |

[a]Migraine Effect = Yes if $AUC_{0-4(migraine)}/AUC_{0-4(migraine\ free)}$ <0.80 and $C_{max(migraine)}/C_{max(migraine\ free)}$ <0.80 after oral dosing.
[b]One subject was excluded of $AUC_{0-inf}$ summary due to poor linearity of the terminal phase (% $AUC_{0-inf}$ extrapolation >20%.

these events were mild in severity. All events resolved after patch removal. Skin irritation assessments, shown in Table 8, fully resolved in most subjects within 12 hours after patch application.

The criteria for a qualifying study migraine were as follows: headache pain must be moderate (score of 2) or severe (score of 3), and the subject has not taken an analgesic or antiemetic medication for the previous 8 hours.

TABLE 8

| | | N (%) Subjects by Skin Assessment Site | | | |
|---|---|---|---|---|---|
| Time Point | Finding | Period 5 | | Period 6 | |
| Pre-dose | No erythema | 18 (100) | | 18 (100) | |
| | | Under Drug Pad | Under Salt Pad | Under Drug Pad | Under Salt Pad |
| At the time of patch removal | No erythema | 0 | 14 (77.8) | 1 (5.6) | 15 (83.3) |
| | Minimal erythema | 13 (72.2) | 4 (22.2) | 17 (94.4) | 3 (16.7) |
| | Moderate erythema | 5 (27.8) | 0 | 0 | 0 |
| 6 hours post-dose | No erythema | 0 | 17 (94.4) | 1 (5.6) | 16 (88.9) |
| | Minimal erythema | 15 (83.3) | 1 (5.6) | 17 (94.4) | 2 (11.1) |
| | Moderate erythema | 3 (16.7) | 0 | 0 | 0 |
| 12 hours post-dose | No erythema | 0 | 17 (94.4) | 1 (5.6) | 16 (88.9) |
| | Minimal erythema | 16 (88.9) | 1 (5.6) | 17 (94.4) | 2 (11.1) |
| | Moderate erythema | 2 (11.1) | 0 | 0 | 0 |
| 48 hours post-dose | No erythema | 7 (38.9) | 18 (100) | 4 (22.2) | 18 (100) |
| | Minimal erythema | 11 (61.1) | 0 | 14 (77.8) | 0 |
| | Moderate erythema | 0 | 0 | 0 | 0 |
| 72 hours post-dose | No erythema | 11 (61.1) | 17 (94.4) | 7 (38.9) | 18 (100) |
| | Minimal erythema | 7 (38.9) | 1 (5.6) | 11 (61.1) | 0 |
| | Moderate erythema | 0 | 0 | 0 | 0 |

Example 2

The Efficacy and Tolerability of a Sumatriptan Iontophoretic Transdermal Patch in the Treatment of Acute Migraine: A Randomized, Double-Blind, Placebo-Controlled Study Objective: The primary objective of this study was to assess the proportion of subjects who are headache pain free at two hours after patch activation. However, key secondary objectives are to assess the proportion of subjects who are nausea free at 2 hours after patch activation, the proportion of subjects who are photophobia free at 2 hours after patch activation as well as the proportion of subjects who are phonophobia free at 2 hours after patch activation.

Other secondary objectives are to assess the proportion of subjects who are headache pain free, who experience headache pain relief, who are nausea free, who are photophobia free and who are phonophobia free at each time point after patch activation. Additional secondary objectives are to assess the proportion of subjects who are migraine free (no headache pain, no nausea, no phonophobia and no photophobia), at two hours after patch activation, the proportion of subjects with a sustained headache pain free response (defined as 2 to 24 hour period) following patch activation without the use of rescue medication, as well as the proportion of subjects who do not use rescue medication within a 24 hour period following patch activation.

Methodology/Study Design: This was a randomized, parallel group, double-blind, placebo controlled study. Subjects will complete three study visits; Screening Visit, Randomization Visit, and Final Visit. Adult subjects who meet the enrollment criteria were randomized in a 1:1 ratio into one of two treatment groups: sumatriptan iontophoretic transdermal patch, or placebo iontophoretic transdermal patch. Dose timing (t=0) for both groups began when the patch was applied and activated. Screening assessments were performed during the Screening During and after a qualifying migraine headache for which the subject uses the study patch, the following steps were performed by the subject:

The subject confirmed that they did not take an analgesic (pain) or antiemetic (anti-nausea) medication for 8 hours prior to using the study patch.

The subject completed the assessments just prior to applying the patch: whether headache is unilateral (one sided) or bilateral (both sides), increases with movement, severity of headache pain, absence or presence of aura, nausea, photophobia (sensitivity to light) and phonophobia (sensitivity to sound).

The subject applied the patch to right or left upper arm and recorded patch application location in the diary.

The subject completed assessments for the presence or absence of pain (assessment of severity if present) as outlined in Table 9, and the absence or presence of nausea, photophobia (sensitivity to light) and phonophobia (sensitivity to sound) at 0.5, 1, 2, 3, 4, 6, 12 and 24 hours after activating the patch. Subjects were required to stay awake to record pain and symptom assessments for the first four hours post patch activation and were instructed to awaken intermittently to complete the 6, 12 and 24 hour assessments. Subjects were encouraged to use the timer provided to ensure that assessment are completed and recorded in the diary at the specified times.

The subject does not use pain medications or medications to treat nausea for the first two hours following patch activation.

At each of the assessment time points, the subject recorded the use of medication to treat pain and/or medication to treat nausea taken through 24 hours following patch activation. Although prohibited, in the event pain medication or medication to treat nausea were taken within the 8 hours prior to patch application, this information was also recorded.

Triptans were not allowed until after the Final Visit and pain medication was allowed 2 hours following patch activation only if the headache pain was moderate or severe.

Medications to treat nausea were allowed 2 hours after patch activation if symptoms were not amenable to supportive measures, and were severe enough to require treatment with a medication.

The subject recorded whether the headache returned (if headache was gone at 2 hours) within 2-24 hours post patch activation.

Patch was gently removed at 4 hours after patch activation (when the LED light is off).

The subject completed self-skin examination at 4 hours (within 10 minutes of patch removal), 6, 12, 24 hours post patch activation and daily thereafter until the self-skin examination score was zero. The self examination irritation scores are found in Table 10.

If the skin irritation score is noted to be a 3 or 4, or worsened after a period of improvement the subject called the Study Doctor or investigative personnel to be seen as soon as possible (within 24 hours).

The subject called within 12 hours of activating the patch and recorded if nausea was absent or present just prior to study patch application.

TABLE 9

Subject Diary Headache Pain Severity Score

| Score | Definition |
|---|---|
| 0 | No pain |
| 1 | Mild pain: allowing normal activity |
| 2 | Moderate pain: disturbing, but not preventing normal activity |
| 3 | Severe pain: normal activity has to be discontinued, bed rest may be necessary |

TABLE 10

Subject Self-Examination Irritation Score

| Score | Definition |
|---|---|
| 0 | No redness |
| 1 | Minimal skin redness |
| 2 | Moderate skin redness with sharp borders |
| 3 | Intense skin redness with or without swelling |
| 4 | Intense skin redness with blisters or broken skin |

Subjects remained in the study until they treated one migraine headache with a study patch or two months after randomization, whichever occurs first. At the final visit, the Investigator examined the subject patch placement site and scored the skin irritation using the scores in Table 2 (above in Example 1). For subjects who had a skin irritation score ≥1 at the final visit, the Investigator scheduled a follow-up visit in 10 days (±2 days) to complete another skin irritation examination and continued to follow the subject weekly thereafter until the skin irritation score was zero (0).

Selection of Study Populations:

Inclusion Criteria: Subjects met all of the criteria outlined above in connection with Example 1.

Results: A total of 530 subjects were randomized (265 in each treatment group), 469 of whom applied the study patch (234 with sumatriptan and 235 placebo). 454 subjects applied and activated (light continuously on for any length of time) the study patch and had at least one post baseline assessment for pain.

Among the 454 subjects, a higher proportion who received the sumatriptan patch were headache pain-free 2 hours after patch activation compared with placebo (18% vs 9%, respectively; P=0.0092). A significant difference from placebo was also observed at 1 hour and continued for all subsequent time points up to and including 12 hours after patch activation (P≤0.0357).

The sumatriptan patch was also associated with a significantly higher proportion of subjects reporting headache pain relief as early as 1 hour following patch activation compared with placebo (29% vs 19%, respectively; P=0.0135). This difference from placebo was maintained at 2 hours (53% vs 29%; P<0.0001) and for all subsequent time points up to and including 12 hours (P<0.01).

Two hours after patch activation, a higher proportion of subjects who received the sumatriptan patch compared with those who received placebo were also nausea-free (84% vs 63%, respectively; P<0.0001), photophobia-free (51% vs 36%, respectively; P=0.0028), and phonophobia-free (55% vs 39%, respectively; P=0.0002).

Figure 7:
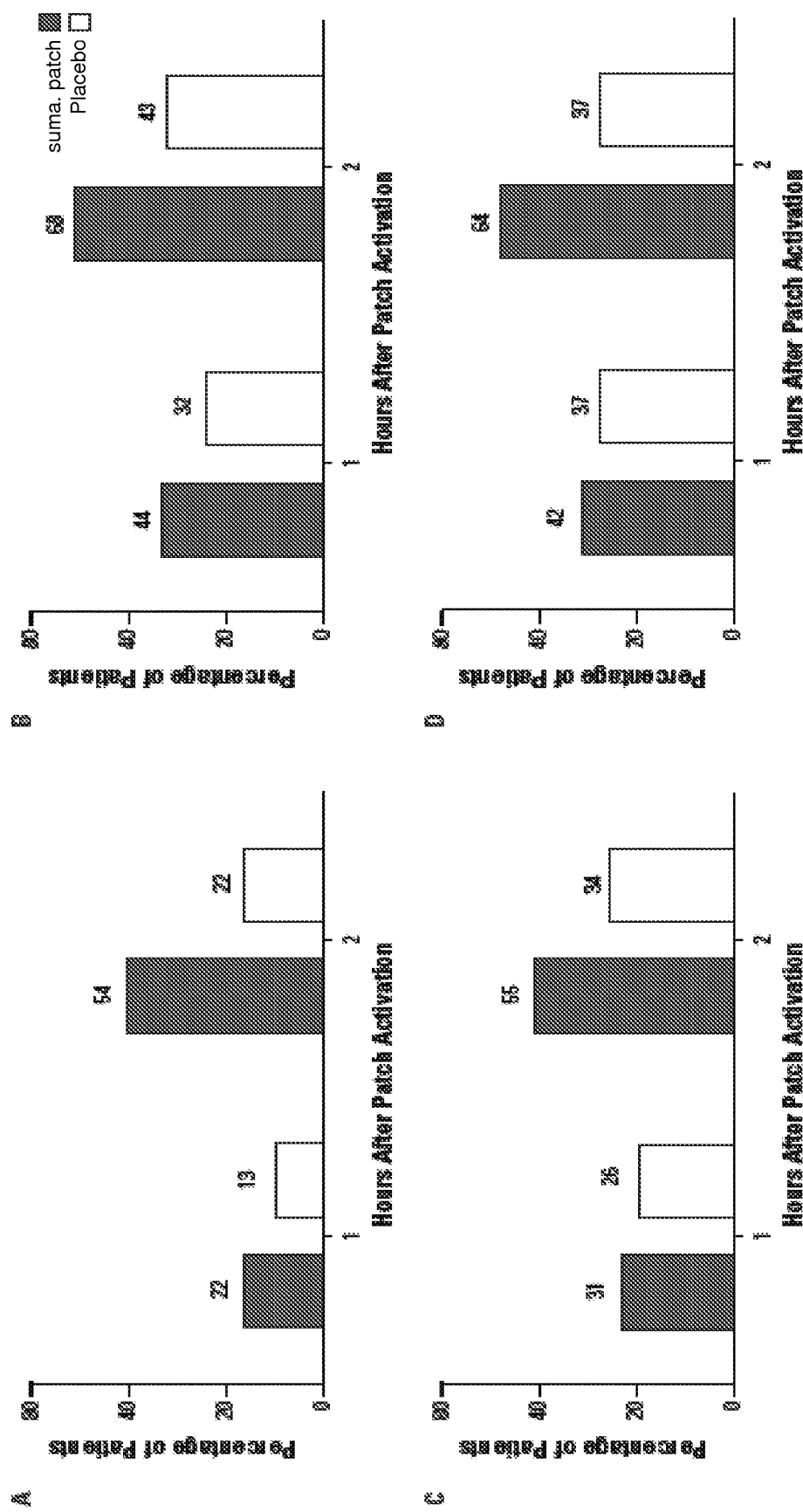
FIGS. 7A-D are graphs illustrating percentage of subjects with nausea at baseline who experienced headache pain relief (A), freedom from nausea (B), freedom from photophobia (C), and freedom from phonophobia (D) 1 and 2 hours after patch activation.

Among subjects who reported nausea at baseline, a higher proportion of those treated with the sumatriptan patch compared with placebo experienced pain relief at 1 hour (22% vs 13%, respectively) and 2 hours (54% vs 22%, respectively) after patch activation (FIG. 7A). Among subjects who reported nausea at baseline, a higher proportion of those treated with the sumatriptan patch compared with placebo were nausea-free at 1 hour (44% vs 32%, respectively) and 2 hours (68% vs 43%, respectively) after patch activation (FIG. 7B). Among subjects who reported nausea at baseline, a higher proportion of those treated with the sumatriptan patch compared with placebo were free from photophobia at 1 hour (31% vs 26%, respectively) and 2 hours (55% vs 34%, respectively) after patch activation (FIG. 7C). Among subjects who reported nausea at baseline, a higher proportion of those treated with the sumatriptan patch compared with placebo were free from phonophobia at 1 hour (42% vs 37%, respectively) and 2 hours (64% vs 37%, respectively) after patch activation (FIG. 7D).

Among the subjects who activated the patch (n=469), treatment-emergent adverse were reported by 50% of subjects who received the sumatriptan patch and 44% of subjects who received placebo. The most common adverse events (≥5% of subjects) were application site-related, and typically resolved within 2 days. These included application site pain (sumatriptan patch 23%; placebo 15%), paresthesia (sumatriptan patch 12%; placebo 19%), pruritus (sumatriptan patch 8%; placebo 7%), and reaction (sumatriptan patch 7%; placebo 6%). The incidence of triptan-specific adverse events typically associated with sumatriptan plasma levels >50 ng/mL was very low in the sumatriptan patch group (3%). 2% of patients in the sumatriptan patch group and 1% of patients in the placebo group discontinued owing to adverse events. Skin irritation data is provided in Tables 11 and 12, below.

TABLE 11

Patient Assessment of skin irritation

| | Suma. Patch | Placebo |
|---|---|---|
| Patch Removal | 39% - none or minimal | 73% - none or minimal |
| | 55% - moderate | 24% - moderate |
| 24 hrs after removal | 79% - none or minimal | 93% - none or minimal |
| | 19% - moderate | 6% - moderate |

TABLE 12

Investigator Assessment of skin irritation at 24-72 hours post patch application

| | Suma. Patch | Placebo |
|---|---|---|
| No or minimal erythema | 88% | 96% |
| Moderate | 11% | 3% |
| Intense | 1% | 1% |

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The contents of all references, patents and patent applications cited throughout this application are hereby incorporated by reference.

We claim:

1. A method for treating nausea in a subject suffering from a migraine, the method comprising: iontophoretically administering an effective amount of a triptan compound to a subject suffering from a migraine, such that the nausea is treated without cardiovascular side effects, wherein the triptan compound is administered iontophoretically in a two phase manner, comprising:
   a first phase, wherein the triptan compound is administered with a current of about 4 mA for about an hour; and
   a second phase, wherein the triptan compound is administered with a current of about 2 mA for about three hours.

2. The method of claim 1, wherein the current does not substantially irritate the subject's skin.

3. The method of claim 1 or claim 2, wherein the current does not result in a skin erythema score of greater than 2.5, of greater than 2.0, of greater than 1.5, or of greater than 1.0, immediately after patch removal.

4. The method of claim 1, wherein the subject is a human.

5. The method of claim 1, wherein the subject is suffering from a prodromal migraine symptom, and wherein the prodromal migraine symptom is treated.

6. The method of claim 1, wherein the subject is suffering from a migraine aura, and wherein the migraine aura is treated.

7. The method of claim 1, wherein the nausea is reduced in the subject by at least about 50%.

8. The method of claim 1, wherein the nausea is treated without migraine-associated absorption reduction.

9. The method of claim 1, wherein the migraine is aborted in the subject.

10. The method of claim 1, wherein the nausea is treated without triptan side effects.

11. The method of claim 1, wherein the nausea is treated for at least two hours.

12. The method of claim 1, wherein the migraine is treated for at least two hours.

13. The method of claim 1, wherein the subject is suffering from a migraine with a pain severity score of 2 or 3.

14. The method of claim 1, wherein the subject is suffering from migraine induced nausea or vomiting.

15. The method of claim 1, wherein the triptan compound is a sumatriptan or a pharmaceutically acceptable salt thereof.

16. The method of claim 15, wherein the subject's headache score is reduced from a score of about 3 to about 2, to about 1, or to about 0.

17. The method of claim 15, wherein the subject's headache score is reduced from a score of about 2 to about 1, or to about 0.

18. The method of claim 15, wherein iontophoretically administering the triptan compound comprises a current which results in minimal or no erythema.

* * * * *